United States Patent
Boys

(10) Patent No.: US 8,075,505 B2
(45) Date of Patent: *Dec. 13, 2011

(54) MASSAGE DEVICE UTILIZING AN UNANCHORED MAGNET FOR PRIMARY FORCE GENERATION

(75) Inventor: Mark A. Boys, Aromas, CA (US)

(73) Assignee: SoundStarts, Inc., Aromas, CA (US)

( * ) Notice: Subject to any disclaimer, the term of this patent is extended or adjusted under 35 U.S.C. 154(b) by 988 days.

This patent is subject to a terminal disclaimer.

(21) Appl. No.: 11/855,315

(22) Filed: Sep. 14, 2007

(65) Prior Publication Data

US 2008/0004552 A1    Jan. 3, 2008

Related U.S. Application Data

(63) Continuation of application No. 11/280,602, filed on Nov. 15, 2005, now Pat. No. 7,270,640.

(60) Provisional application No. 60/666,328, filed on Mar. 29, 2005.

(51) Int. Cl.
*A61H 1/00* (2006.01)

(52) U.S. Cl. ........................... 601/78; 601/79

(58) Field of Classification Search .............. 601/78–79; 600/587, 16–17
See application file for complete search history.

(56) References Cited

U.S. PATENT DOCUMENTS

| | | | | |
|---|---|---|---|---|
| 4,464,634 A * | 8/1984 | Velazquez | | 330/264 |
| 5,003,517 A * | 3/1991 | Greer, Jr. | | 367/178 |
| 6,155,967 A * | 12/2000 | Catlett | | 600/15 |
| 6,251,061 B1 * | 6/2001 | Hastings et al. | | 600/16 |
| 6,582,661 B1 * | 6/2003 | Pardue et al. | | 422/68.1 |
| 7,270,640 B2 * | 9/2007 | Boys | | 601/78 |
| 2004/0002665 A1 * | 1/2004 | Parihar et al. | | 600/587 |

* cited by examiner

*Primary Examiner* — Michael A. Brown
(74) *Attorney, Agent, or Firm* — Donald R. Boys; Central Coast Patent Agency, Inc.

(57) ABSTRACT

A therapeutic system for massage comprises a massage device having an activation cell comprising a hollow pocket at least partially filled with a ferro-magnetic fluid, a permanent magnet suspended in the ferro-magnetic fluid, a coil of electrically-conductive material in proximity to the pocket, and a connection interface to connect the coil to a source of varying voltage and current, and a power source of varying voltage for connecting to the connection interface to drive the activation cell.

27 Claims, 5 Drawing Sheets

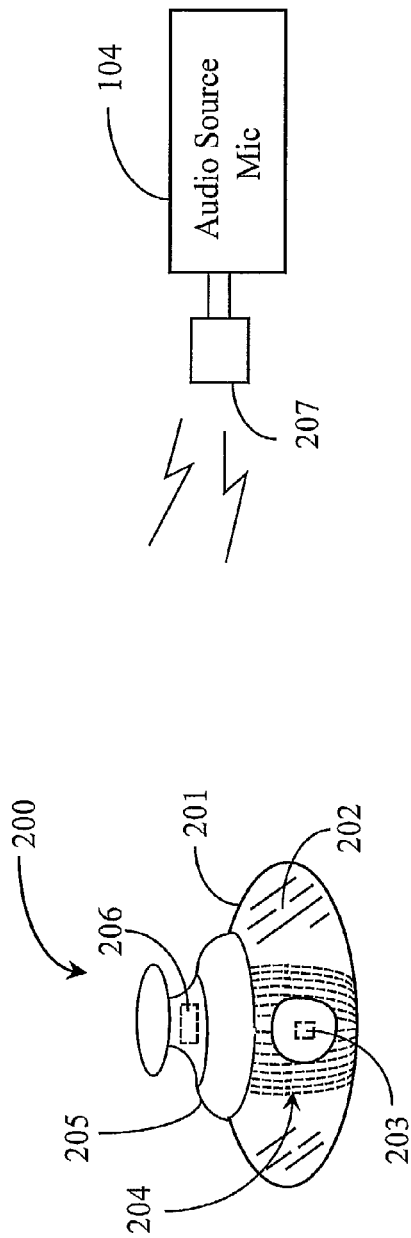
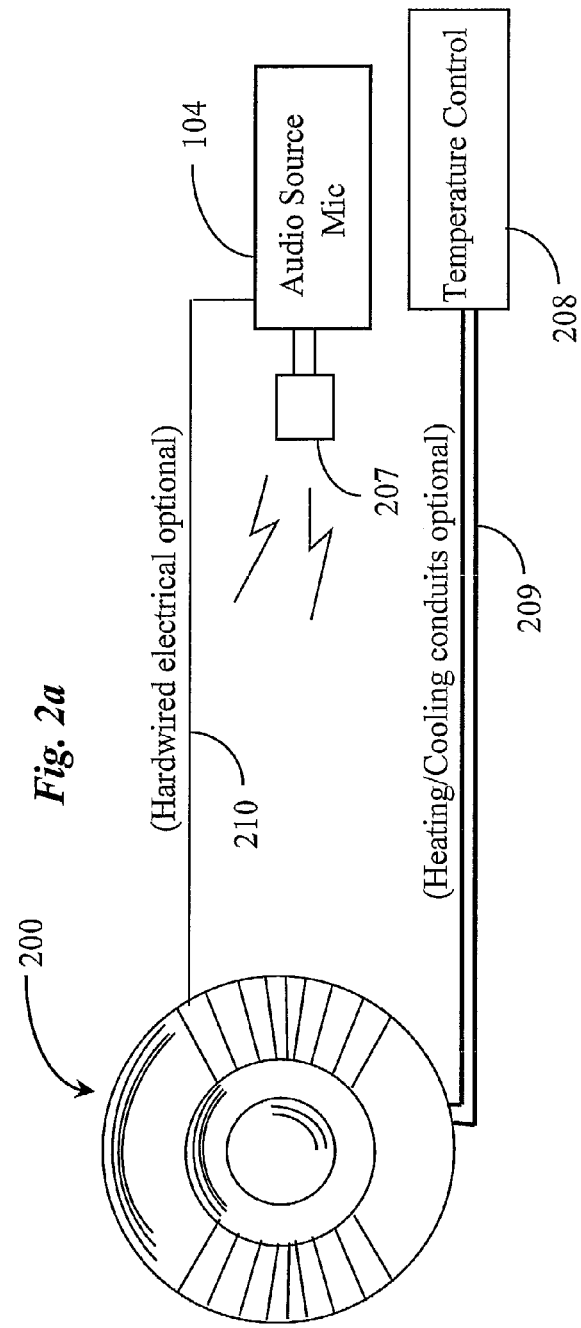

MASSAGE DEVICE UTILIZING AN UNANCHORED MAGNET FOR PRIMARY FORCE GENERATION

CROSS-REFERENCE TO RELATED APPLICATIONS

The present application is a continuation application of copending patent application Ser. No. 11/280,602, filed on Nov. 15, 2005, which claims priority to provisional patent application Ser. No. 60/666,328, filed Mar. 29, 2005, and which are incorporated herein in their entirety by reference.

BACKGROUND OF THE INVENTION

1. Field of the Invention

The present invention is in the area of devices for assistance in performing massage and other topical procedures on living bodies, and pertains more particularly to the way force and vibration is generated in such devices, and the integration of audio with such generation in addition to magnetic wave therapy.

2. Discussion of the State of the Art

Massage devices of many sorts and designs are well-known in the art, and conventional massage devices use an offset weighting of a shaft or armature with an electric motor to generate oscillating forces, which causes reciprocal translation of at least a portion of the device. An unbalanced weight on a rotating portion of the motor, or on an apparatus driven by the motor, generates centripetal force in a constantly-changing direction, which translates to reciprocating movement of the motor or apparatus. This reciprocating motion can be translated to an outer frame member or shell which may be used to contact a portion of a body to accomplish massage or other topical treatment or procedure.

SUMMARY OF THE INVENTION

In an embodiment of the invention a massage device is provided comprising an activation cell having a hollow pocket or enclosure at least partially filled with a ferro-magnetic fluid, a permanent magnet suspended in the ferro-magnetic fluid, a coil of electrically-conductive material in proximity to the pocket, and a connection interface to connect the coil to a power source of varying voltage.

In one embodiment the device is shaped for application to a portion of a human body. Also in an embodiment there may be internal conduits for fluid, and an interface to external conduits for delivering temperature-controlled fluid for controlling the temperature of the device. Also in an embodiment there may be means of controlling the temperature of the device electrically as opposed to a fluid transfer, such as with peltier effect devices or resistive devices.

In some embodiments the device is contoured to a human face, and in some other embodiments to fit over a human limb or shoulder. In some embodiments the device is shaped to be inserted in a human bodily orifice.

In some embodiments there are two or more activation cells, and some of these embodiments there is further circuitry and selection elements for driving activation cells independently.

In another embodiment of the invention a therapeutic system is provided having a massage device comprising an activation cell with a hollow pocket at least partially filled with a ferro-magnetic fluid, a permanent magnet suspended in the ferro-magnetic fluid, a coil of electrically-conductive material in proximity to the pocket, and a connection interface to connect the coil to a source of varying voltage and current, and a power source of varying voltage for connecting to the connection interface to drive the activation cell.

In some embodiments the device is shaped for application to a particular portion of a human body. Also in some embodiments there may be internal conduits for fluid, and an interface to external conduits for delivering temperature-controlled fluid for controlling the temperature of the device.

In some cases the device is contoured to a human face. In other cases the device may be contoured to fit over a human limb or shoulder. In still other cases the device may be shaped to be inserted in a human bodily orifice.

In some embodiments there are two or more activation cells, and these may separately controlled through circuitry and selection elements for driving activation cells independently.

In some embodiments of the system the power source may be an amplifier for amplifying and providing audio signals as output. In such embodiments the power source may provide audio signals, and one or more outer surface of the device may be translated by the activation cell, providing vibration for massage treatment and acting also as speaker elements, causing vibrations in the surrounding air as audible sound according to the audio input.

In yet another embodiment of the present invention a method for practicing vibratory massage is provided, comprising steps of (a) providing an activation cell in a device having outer surfaces applicable to a human body, the cell comprising a hollow pocket at least partially filled with a ferro-magnetic fluid, a permanent magnet suspended in the ferro-magnetic fluid, a coil of electrically-conductive material in proximity to the pocket, and a connection interface to connect the coil to a source of varying voltage and current; and (b) driving the coil by a power source of varying voltage connected to the connection interface.

In some embodiments of the method, in step (a) the surfaces are shaped for application to a particular portion of a human body. Also in some embodiments there may be a further step (c) for controlling temperature of the device through internal conduits for fluid in the device, and an interface to external conduits for delivering temperature-controlled fluid for controlling the temperature of the device. Also in an embodiment there may be means of controlling the temperature of the device electrically as opposed to with a fluid transfer, such as with peltier effect devices or resistive devices.

In some cases the particular portion of the body may be a human face. In some other embodiments the particular portion of the human body may be a human limb or shoulder. In still other embodiments the particular portion of the human body may be a human body orifice.

In some embodiments of the method there may be two or more activation cells, and in some of these there may be further steps for using circuitry and selection elements for driving activation cells independently.

In some embodiments of the method the power source may be an amplifier for amplifying and providing audio signals as output, and in such embodiments the power source may provide audio signals, and one or more outer surface of the device may be translated by the activation cell or cells, providing vibration for massage treatment and acting also as speaker elements, causing vibrations in the surrounding air as audible sound according to the audio input.

BRIEF DESCRIPTION OF THE DRAWING FIGURES

FIG. 2a illustrates a device according to an embodiment of the present invention shaped to be useful for general massage practice, such as might be applied to larger expanses of a human body.

FIG. 2b is a top view of the device of FIG. 2a, to better illustrate shape and placement of components.

DETAILED DESCRIPTION

Figure 1:
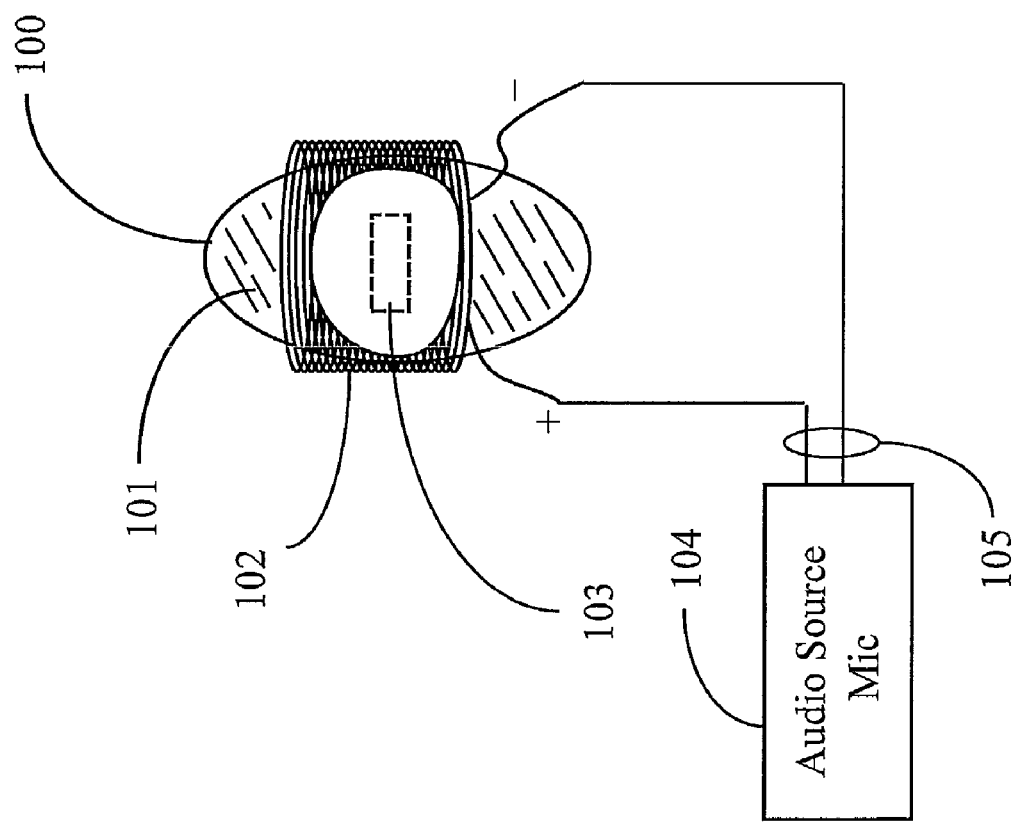
FIG. 1 is a mostly schematic illustration showing how reciprocating motion may be produced in an embodiment of the present invention.

FIG. 1 is a mostly schematic illustration showing generally how reciprocating motion may be produced in an embodiment of the present invention for a massage or topical treatment device. In this example a closed-container 100, in this case having a roughly egg shape, is at least partially filled with a ferro-magnetic fluid 101. Preferably the fluid completely fills the internal volume of the container, although in some cases partial filling may be used to dampen some effects to be described below. Such ferro-magnetic fluids may be prepared in the art by mixing a finely-ground ferro-magnetic material, like iron, for example, in a liquid or semi-liquid vehicle, such as viscous oil. A permanent magnet 103 is enclosed in the container with the ferro-magnetic fluid 101, and will typically maintain a supported position by nature of the static magnetic field around the permanent magnet and its interaction with the ferro-magnetic fluid. The nature of the suspension and positioning of the permanent magnet in the fluid in the container may be influenced by a number of factors, such as the strength of the permanent magnet, the weight and size of the magnet, the nature of the fluid, and the size and shape of the container.

A coil 102 of a number of turns of electrically conductive material, which may be round or flattened wire or ribbon material, is wrapped around container 100, and the ends of the coil are connected to output 105 of an audio source 104, which may be an audio amplifier. The output of such an audio source is typically used for driving a coil in a conventional fabric-enabled speaker.

In operation of a conventional audio system in which one or more conventional speakers may be connected to audio output from an amplifier, a varying driving voltage is impressed across the terminals of the output 105, causing a varying current in a coil in the vicinity of a magnet typically rigidly connected to a fabric speaker cone. The varying current in the coil causes a varying magnetic field to be created, which is focused by the coil and whose strength is determined by spacing and turn-density of the coil. The permanent magnet in the vicinity of the coil is caused to oscillate, following the frequencies and strength of the field created by the coil by virtue of the varying current in the coil. Since the varying field is created by recorded audio, movement of the fabric speaker rigidly connected to the permanent magnet creates pressure waves in the air that are the sound that human ears pick up. The system reproduces the originally recorded audio, such as instrumental music and lyrics from a human voice.

In the present case the output 105 drives coil 102 formed around container 100 affects permanent magnet 103, which is suspended and supported in ferro-magnetic fluid 101 in container 100. Just as in a conventional speaker the coil, by nature of the varying voltage and resultant current, creates a dynamic magnetic field in the region of suspended permanent magnet 103. This driving voltage may be impressed as the audio output of source 104 in the form of music or voice.

In embodiments of the present invention the suspended permanent magnet oscillates, and moving as it does in an essentially incompressible fluid, causes varying force to be applied to the inside walls of container 100, and this varying force causes reciprocation of the container. Container 100 vibrates just as the fabric of a conventional speaker might vibrate, but now the vibration can also be used for massage and other topical treatment purposes as well as creating a replication of the originally-recorded music or other audio phenomenon.

There is a three-fold effect. One effect is that the relatively rigid container walls acts as a speaker membrane, making audible whatever music or voice has been impressed upon coil 102; the second effect is the effect of movement of the container, and anything that might be fastened to it. This movement, by inclusion of appropriate elements, can be used as a massage device, whereby a person may enjoy a massage experience in synchronization with the music that is sent to the coil; the third effect is the potentially beneficial effect of the magnetic fields of the device, both from the permanent magnet or magnets in the device and the fields from the coil or coils used to manipulate the permanent magnet or magnets. The effects of expanding and contracting magnetic fields on the human body or portions of a person's body are not well-known, but it is generally agreed that expanding and contracting magnetic fields may have beneficial effects for such purposes as pain alleviation, increased blood circulation in healing areas of the body as well as pain alleviation and management.

In the case of the apparatus of FIG. 1, one might embed the coil in the container wall, or cover the coil with a top-coating material to protect the coil wires, and grasp the egg-shaped container to be pressed against expanses of flesh of a human, using the device as a massage tool. A unique feature of the tool being that the device provides audio output completely synchronized with the vibrating effects used for massage purposes. A massage therapist, as is well-known, often plays soothing music during a session of body massage. With a device according to an embodiment of the present invention the device itself plays the music, and the action of the device is in concert with the music.

FIG. 2a illustrates a device 200 according to an embodiment of the present invention shaped to be useful for general massage practice, such as might be applied to larger expanses of a human body. Device 200 has a container space 201 filed with a ferro-magnetic fluid 202, a driving coil 204 and a suspended permanent magnet 203. In this case the output 105 of the amp 104 goes to a wireless transmission device 207, which transmits to a receiver 206. Although not shown, device 200 in this case also has a local power supply, such as a replaceable or rechargeable battery. Receiver 206 and associated circuitry drives coil 204, which drives magnet 203 in turn. As before, the outer shell of the device becomes a resonator, essentially a speaker, and also serves as a surface for vibration for massage.

FIG. 2b is a top view of device 200 of FIG. 2a, to better illustrate shape and placement of components. Device 200 in this embodiment is round rather than egg-shaped, and has the aspect of a stone. In one embodiment device 200 is constructed such that all internal components are encapsulated hermetically, and the entire device may be heated or cooled before use to provide yet an additional therapeutic topical effect. In other embodiments, the device may be connected by hardwire, as shown by optional path 210 in FIG. 2b, and there may additionally be one or more conduits 209 from a temperature control source 208 for heated or cooled liquid to heat or cool the device while the device is in use.

Figure 2C:
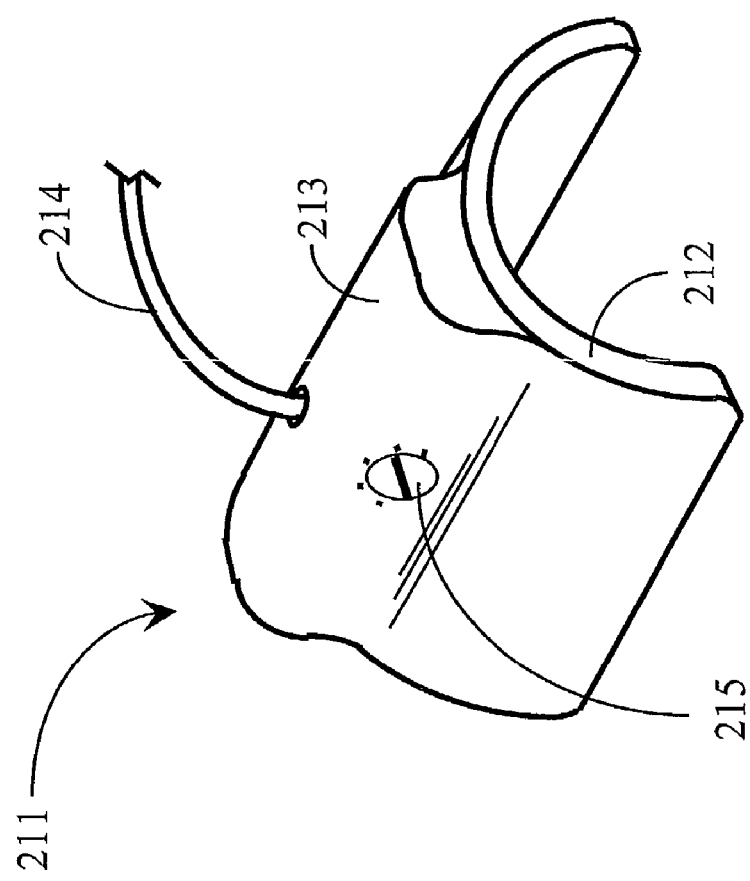
FIG. 2c illustrates a device according to an embodiment of the present invention shaped to be useful for general massage practice applied to a sharply curved portion of a human body.

FIG. 2c illustrates a device according to an embodiment of the present invention shaped to be useful for general massage practice applied to a sharply curved portion of a human body. Device 211 has an application portion 212 shaped as a length of a split tubing, and is applicable to, for example, a subject's arm, leg, shoulder, etc. An adjacent raised portion 213 houses interface circuitry for connecting incoming signals (delivered through conductors in conduit 214, or received from a wireless transmitter) to one or more coils in the device for generating magnetic fields to affect permanent magnets suspended in ferro-magnetic fluid in the device. In some embodiments there are separate pockets in the device filled with ferro-magnetic fluid, and each pocket has a surrounding activation coil and a small permanent magnet suspended in the fluid. Each one of these is an activation cell. In one embodiment there is a selector switch 215 for engaging individual ones of the available cells, or multiple cells in concert. The strength of the incoming signal or signals (there may be more than one set of input conductors, and separate conductors can carry separate signals) and the number engaged and working in concert may affect the nature of the vibration of the device. As with other embodiments described, device 211 may also be heated or cooled to provide additional topical effect. Conduit 214 may have lines for heated or cooled fluid.

Figure 2D:
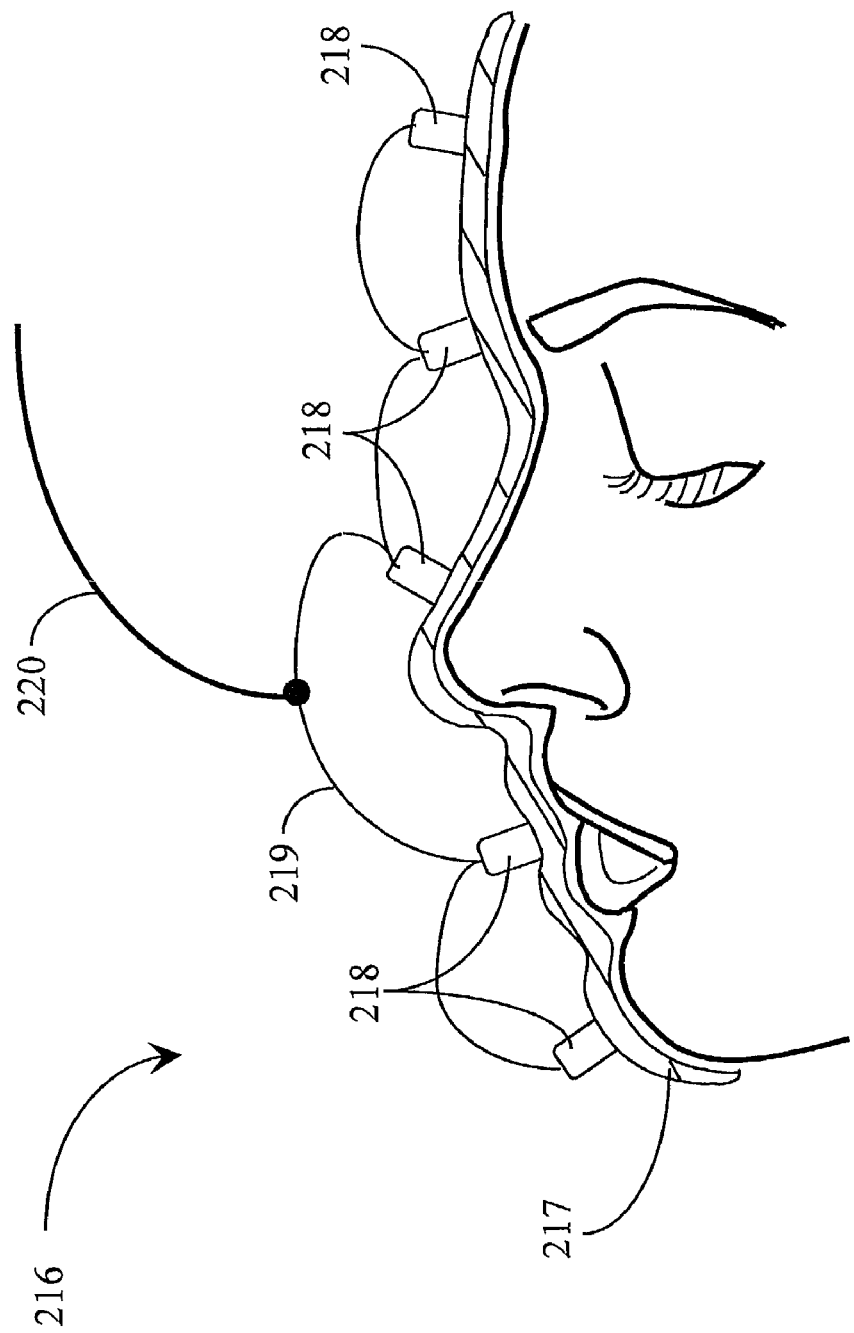
FIG. 2d illustrates a device according to an embodiment of the present invention shaped to be useful for general massage practice applied to a very specific area of a human body.

FIG. 2d illustrates a device according to an embodiment of the present invention shaped to be useful for general massage practice and topical treatment applied to a very specific area of a human body. In this particular embodiment a mask 217 has been made of a woman's face. The mask in this embodiment is of a semi-rigid material, plastic, for example, and is covered on the side applied to the face with a softer material, like a flexible polymer. Several activation cells 218 are affixed to the mask, and each has a hollow interior pocket filled with ferro-magnetic fluid, a coil surrounding the pocket, and a permanent magnet suspended in the fluid. The coils are connected through wiring 219 and through the wiring to a signal system, such an amplifier, through conduit 220. In operation the signal delivered drives the coils associated with each activation cell which provides vibration of the mask by forces transferred through the fluid of each cell to the outer walls of each cell, which are fixed to the rigid part of the mask.

In some embodiments heating and cooling may be applied. Also openings are provided through the mask at least for breathing, and may also be provided at the area of the eyes so a person using the mask can see through the mask. Also in some embodiments cells may be controlled separately or in tandem. The signals provided can be from musical sources, and portions of the mask may also act as speaker elements causing discernable and audible music according to the signals provided.

Figure 2E:
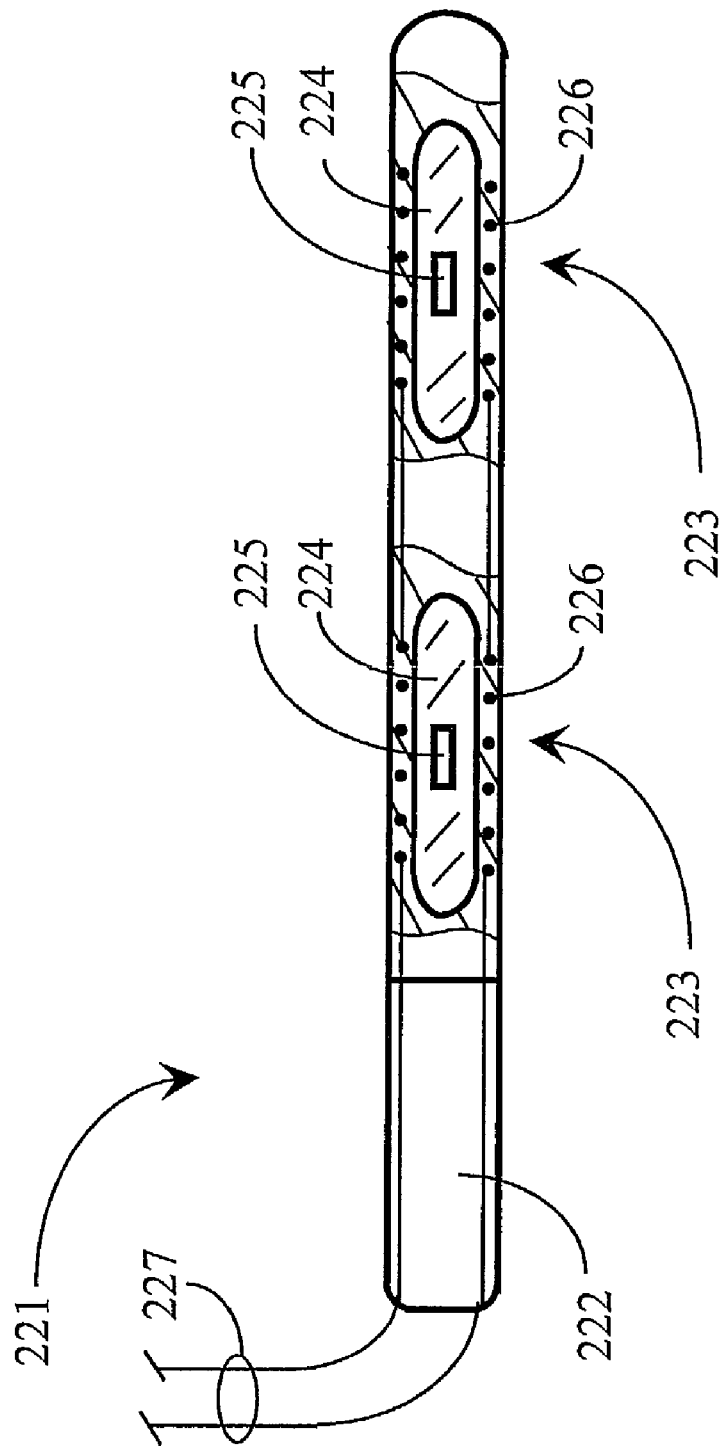
FIG. 2e illustrates a device according to an embodiment of the present invention shaped to be useful for applying to human body orifices for therapeutic purposes.

FIG. 2e illustrates a device according to an embodiment of the present invention shaped to be useful for applying to human body orifices for therapeutic purposes. Device 216 is shaped as a cylinder, and has one or more activation cells 223 at positions along the length. Each activation cell comprises a hollow region 224 filled with ferro-magnetic fluid, a suspended permanent magnet, and a surrounding activation coil. Leads 227 in this embodiment come out of the device at the end of a handle area 222. In this embodiment the activation cells may be wired in a manner to be concurrently or separately controlled, there may be conduits for hot or cold fluid, and the device may have battery power and be activated remotely by wirelessly transmitted signals, as described above for other devices.

The method of creating vibration for such devices by a coil acting on a permanent magnet suspended in a ferro-magnetic fluid provides a number of advantages over conventional ways of creating vibration. The movement of the magnet may be linear, or may move in other patterns depending on the shape and geometry of coils, No motors or bearings are necessary, reducing the manufacturing cost. A strong magnetic field may be present, which according to some, provides certain health benefits in combination with massage, such as increased blood circulation in damaged tissue which may promote healing, and also possible benefits in pain alleviation and management.

A wide variety of vibration patterns may be presented by utilizing a DSP or other electronic means to modify the current flow, and by switching current to different coils, which may be wound within one another. Activation cells can be provided so impetus is provided in different directions. The massage devices may also be connected directly to the output of a microphone to generate vibrations that change in accordance with the frequency of the audio signals. And in many cases the outer walls of devices according to different embodiments of the present invention may act as speaker elements, and create audible sound according to the input signals. One may drive such devices by musical scores, such as rock music, classical music, rap, and essentially any recorded audio. As audio output devices, these devices are not subject to power below a level which would damage the fabric elements of a conventional speaker, but may be driven at any output level supportable by the driving source. In some cases limitations may be imposed for the protection of the person to whom such a device might be applied.

It is emphasized that the embodiments described herein are exemplary only, and many variations and applications of the principles may be made without departing from the spirit and scope of the invention. The scope of the invention is therefore only limited by the scope of the claims that follow.

What is claimed is:

1. A massage device comprising:
    an activation cell comprising a hollow pocket surrounded by a rigid wall, the pocket at least partially filled with a ferro-magnetic fluid, a permanent magnet suspended in the ferro-magnetic fluid, and a coil of electrically-conductive material in proximity to the pocket; and
    a source providing an audio signal of music or voice, or both, to the coil;
    wherein the audio signal causes the permanent magnet to vibrate, translating force to the rigid wall, which acts both as a massage vibrator and as a speaker membrane, the voice or music in concert with the vibration.

2. The device of claim 1 shaped for application to a portion of a human body.

3. The device of claim 2 further comprising internal conduits for fluid, and an interface to external conduits for delivering temperature-controlled fluid for controlling the temperature of the device.

4. The device of claim 2 wherein the device is contoured to a human face.

5. The device of claim 2 wherein the device is contoured to fit over a human limb or shoulder.

6. The device of claim 2 shaped to be inserted in into a human bodily orifice.

7. The device of claim 2 having two or more activation cells.

8. The device of claim 6 further comprising circuitry and selection elements for driving activation cells independently.

9. A therapeutic system comprising:
a massage device comprising an activation cell comprising a hollow pocket surrounded by a rigid wall, the pocket at least partially filled with a ferro-magnetic fluid, a permanent magnet suspended in the ferro-magnetic fluid, and a coil of electrically conductive material in proximity to the pocket; and
a source providing an audio signal of music or voice, or both, to the coil;
wherein the audio signal causes the permanent magnet to vibrate, translating force to the rigid wall, which acts both as a massage vibrator and as a speaker membrane, the voice or music in concert with the vibration.

10. The system of claim 9 wherein the device is shaped for application to a portion of a human body.

11. The system of claim 10 further comprising internal conduits in the device for fluid, and an interface to external conduits for delivering temperature-controlled fluid for controlling the temperature of the device.

12. The system of claim 10 wherein the device is contoured to a human face.

13. The system of claim 10 wherein the device is contoured to fit over a human limb or shoulder.

14. The system of claim 10 shaped to be inserted into a human bodily orifice.

15. The system of claim 10 having two or more activation cells.

16. The system of claim 15 further comprising circuitry and selection elements for driving activation cells independently.

17. A method for practicing vibratory massage, comprising steps of:
(a) providing an activation cell in a device having outer surfaces applicable to a human body, the cell comprising a hollow pocket surrounded by a rigid wall, the pocket at least partially filled with a ferromagnetic fluid, a permanent magnet suspended in the ferro-magnetic fluid, and a coil of electrically-conductive material in proximity to the pocket; and
(b) driving the coil by an audio signal source, wherein the audio signal causes the permanent magnet to vibrate, translating force to the rigid wall, which acts both as a massage vibrator and as a speaker membrane, the voice or music in concert with the vibration.

18. The method of claim 17 wherein, in step (a) the surfaces are shaped for application to a particular portion of a human body.

19. The method of claim 18 further comprising a step (c) for controlling temperature of the device through internal conduits for fluid in the device, and an interface to external conduits for delivering temperature-controlled fluid for controlling the temperature of the device.

20. The method of claim 18 wherein the particular portion of the body is a human face.

21. The method of claim 18 wherein the particular portion of the human body is a human limb or shoulder.

22. The method of claim 18 wherein the particular portion of the human body is a human body orifice.

23. The method of claim 18 wherein, in step (a) there are two or more activation cells.

24. The method of claim 23 further comprising steps for using circuitry and selection elements for driving activation cells independently.

25. A massage device comprising:
two or more activation cells each comprising a hollow pocket at least partially filled with a ferro-magnetic fluid, a permanent magnet suspended in the ferro-magnetic fluid, and a coil of electrically-conductive material in proximity to the pocket;
a connection interface connecting the coil to a power source of varying voltage; and circuitry and selection elements driving the activation cells independently.

26. A therapeutic system comprising:
a massage device comprising two or more activation cells each comprising a hollow pocket at least partially filled with a ferro-magnetic fluid, a permanent magnet suspended in the ferro-magnetic fluid, and a coil of electrically-conductive material in proximity to the pocket;
a connection interface connecting the coil to a power source of varying voltage; and
circuitry and selection elements driving the activation cells independently.

27. A method for practicing vibratory massage, comprising steps of:
(a) providing two or more activation cells in a device having outer surfaces applicable to a human body, the cells each comprising a hollow pocket at least partially filled with a ferromagnetic fluid, a permanent magnet suspended in the ferro-magnetic fluid, a coil of electrically-conductive material in proximity to the pocket, and a connection interface to connect the coils to a source of varying voltage; and
(b) driving the coils independently by circuitry and selection elements.

* * * * *